(12) United States Patent
Davuluri et al.

(10) Patent No.: US 8,871,945 B2
(45) Date of Patent: Oct. 28, 2014

(54) PROCESS FOR PREPARATION OF RUFINAMIDE

(76) Inventors: Ramamohan Rao Davuluri, San Clemente, CA (US); Ravi Ponnaiah, Madurai (IN); Sanjay Kumar Dehury, Hyderabad (IN); Selvaraju K., Namakkal (IN); Deepthi VPSS, Narsapur (IN); Dhanunjaya Naidu, Vizianagaram (IN)

( * ) Notice: Subject to any disclaimer, the term of this patent is extended or adjusted under 35 U.S.C. 154(b) by 0 days.

(21) Appl. No.: 13/818,660

(22) PCT Filed: Aug. 23, 2011

(86) PCT No.: PCT/IN2011/000561
§ 371 (c)(1),
(2), (4) Date: Feb. 23, 2013

(87) PCT Pub. No.: WO2012/025936
PCT Pub. Date: Mar. 1, 2012

(65) Prior Publication Data
US 2013/0184469 A1    Jul. 18, 2013

(30) Foreign Application Priority Data
Aug. 25, 2010 (IN) .......................... 2458/CHE/2010

(51) Int. Cl.
*C07D 249/04* (2006.01)
*C07D 249/06* (2006.01)
*C07C 67/307* (2006.01)
*C07C 51/60* (2006.01)

(52) U.S. Cl.
CPC ............ *C07D 249/06* (2013.01); *C07D 249/04* (2013.01); *C07C 67/307* (2013.01); *C07C 51/60* (2013.01)
USPC ......................................................... 548/255

(58) Field of Classification Search
CPC ..................................................... C07D 249/04
USPC ......................................................... 548/255
See application file for complete search history.

(56) References Cited

U.S. PATENT DOCUMENTS

2013/0045998 A1* 2/2013 Abelino De Leon Martin et al. .............................. 514/359

OTHER PUBLICATIONS

Mudd, Apr. 18, 2010, Tetrahedron Letters, vol. 51, p. 3229-3231.*

* cited by examiner

*Primary Examiner* — Rebecca Anderson
*Assistant Examiner* — Karen Cheng
(74) *Attorney, Agent, or Firm* — Schmeiser, Olsen & Watts, LLP

(57) ABSTRACT

The invention relates to a novel, industrially viable, cost effective process for the preparation of 1-(2,6-difluorobenzyl)-1H-1,2,3-triazole-4-carboxamide commonly known as Rufinamide and intermediates thereof.

13 Claims, No Drawings

PROCESS FOR PREPARATION OF RUFINAMIDE

FIELD OF THE INVENTION

The invention provides a novel, industrially viable, cost effective process for manufacturing methyl 1-(2,6-difluorobenzyl)-1H-1,2,3-triazole-4-carboxylate a key intermediate in the synthesis of Rufinamide.

CROSS REFERENCE TO RELATED APPLICATION

This application is the complete specification and claims priority from the provisional specification No. 2458/CHE/2010 filed on Aug. 25, 2010

BACKGROUND OF THE INVENTION 1-(2,6-difluorobenzyl)-1H-1,2,3-triazole-4-carboxamide commonly known as Rufinamide (Formula I) is triazole derivative and is indicated for adjunctive treatment of seizures associated with Lennox-Gastaut syndrome in children 4 years and older and adults. Rufinamide exerts its antiepileptic effect is unknown. The results of in vitro studies suggest that the principal mechanism of action of Rufinamide is modulation of the activity of sodium channels and in particular, prolongation of the inactive state of the channel. Rufinamide (≥1 μM) significantly slowed sodium channel recovery from inactivation after a prolonged prepulse in cultured cortical neurons, and limited sustained repetitive firing of sodium-dependent action potentials (EC50 of 3.8 μM).

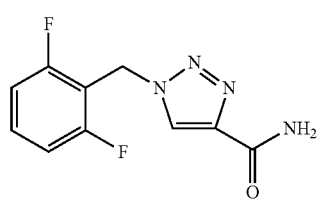

Formula-I

The Rufinamide was first disclosed in U.S. Pat. No. 4,789,680 by Ciba-Geigy Corporation. The synthetic method employed is depicted in the following reaction scheme I.

The process comprises the preparation of Rufinamide by reacting 2,6-difluorobenzyl chloride and sodium azide in the presence of DMSO to obtain 2,6-difluoro benzyl azide, which is then treated with propiolic acid to give carboxylic acid intermediate which on further reaction with thionyl chloride to give corresponding acyl chloride. The acyl chloride intermediate is further reacted with methanolic ammonia to yield Rufinamide.

U.S. Pat. No. 6,277,999 describes the process for the preparation of Rufinamide as shown in Scheme II which comprises coupling of 2,6-difluorobenzyl azide and 2-chloroprop-2-enenitrile in presence of aq. sodium hydroxide and solvent toluene to give Rufinamide.

Scheme II

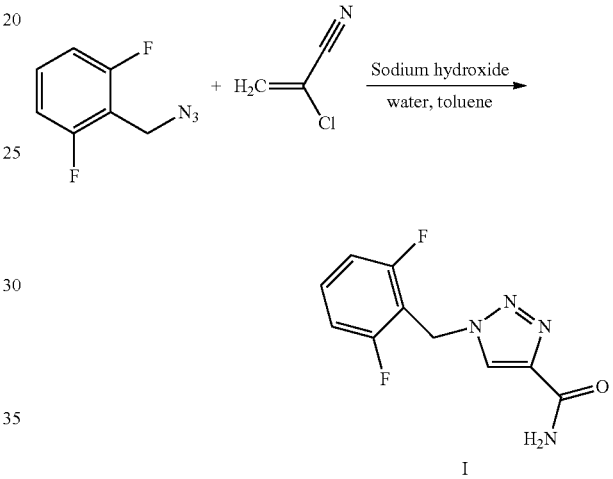

WO 2010/043849 describes the process for the preparation of Rufinamide as shown in scheme III below, which comprises the reaction of 2-(azidomethyl)-1, 3-difluorobenzene with methyl propiolate to obtain methyl 1-(2,6-difluorobenzyl)-1H-1,2,3,-triazole-4-carboxylate and which is reacted with ammonia to yield Rufinamide.

Scheme-I

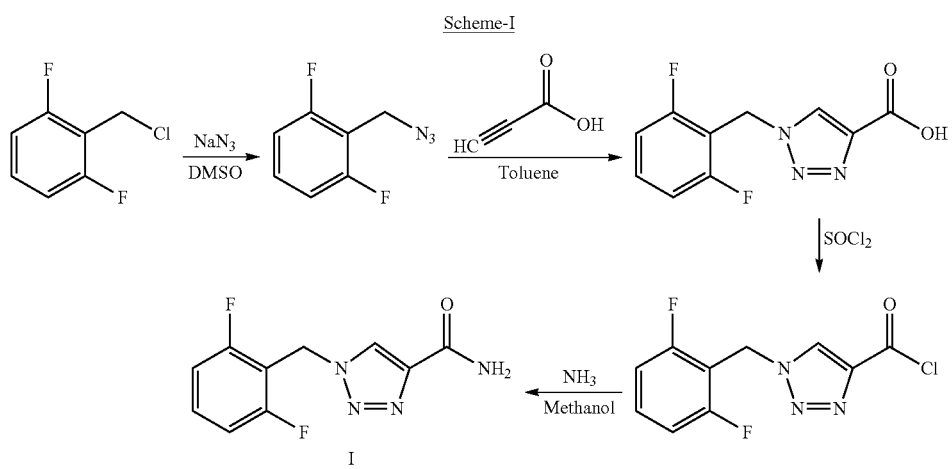

3

Scheme III

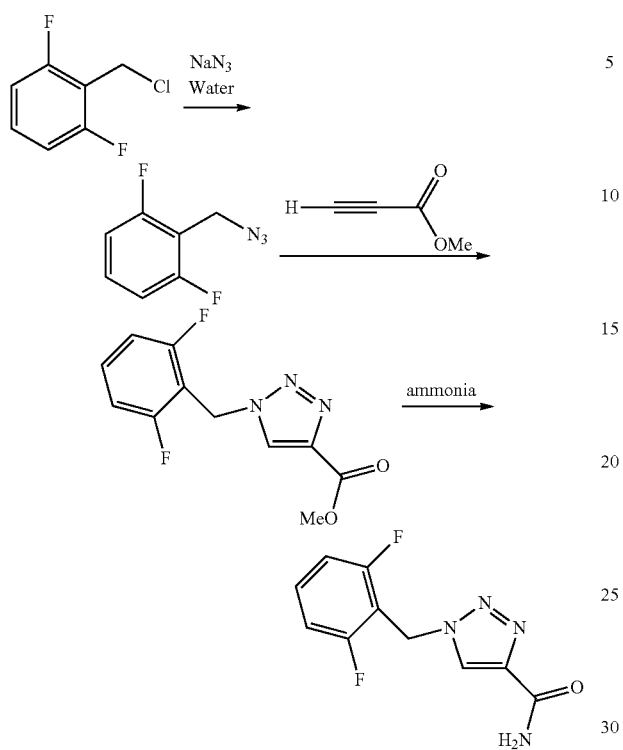

The aforementioned prior art processes involved expensive reagents like propiolic acid and 2-chloroprop-2-enenitrile in their processes and also the reported processes have complexities over yield, control of impurities like 5-carboxylic acid amide and tetrazole impurities during the process and commercial viability. Hence there is a continuous need for novel and effective process for preparing Rufinamide. The present inventors have made extensive researches to discover novel and commercially viable method for preparing Rufinamide with high yield.

SUMMARY OF THE INVENTION

A novel process for the preparation of Rufinamide and its intermediates has been developed. 1-(2, 6-difluorobenzyl)-1H-1,2,3-triazole-4-carboxylate ester of formula VI, a key intermediate in the synthesis of Rufinamide is obtained by the reaction of 2-(azidomethyl)-1,3-difluorobenzyl with alkyl 2-bromoacrylate. The present invention also provides the process for the preparation of 2-bromoacrylate of formula V, which comprises brominating acrylate of formula IV in presence of a brominating agent followed by treatment with base.

The object of the invention is to provide a novel process for the preparation of Rufinamide.

Another object of the present invention is to provide a process for the preparation of 1-(2,6-difluorobenzyl)-1H-1,2,3-triazole-4-carboxylate ester of formula VI, a key intermediate in the preparation of Rufinamide.

Yet another object of the invention is to provide a process for the bromination of alkyl acrylate of formula IV to obtain alkyl 2-bromoacrylate of formula V which is being used in the present synthesis of Rufinamide.

4

DESCRIPTION OF THE INVENTION

In accordance with the present invention 1-(2,6-difluorobenzyl)-1H-1,2, 3-triazole-4-carboxylate ester of formula VI, a key intermediate in the synthesis of Rufinamide is obtained by the reaction of 2-(azidomethyl)-1,3- difluorobenzyl with alkyl 2-bromoacrylate. The process of the invention is depicted in following scheme-IV.

Scheme-IV

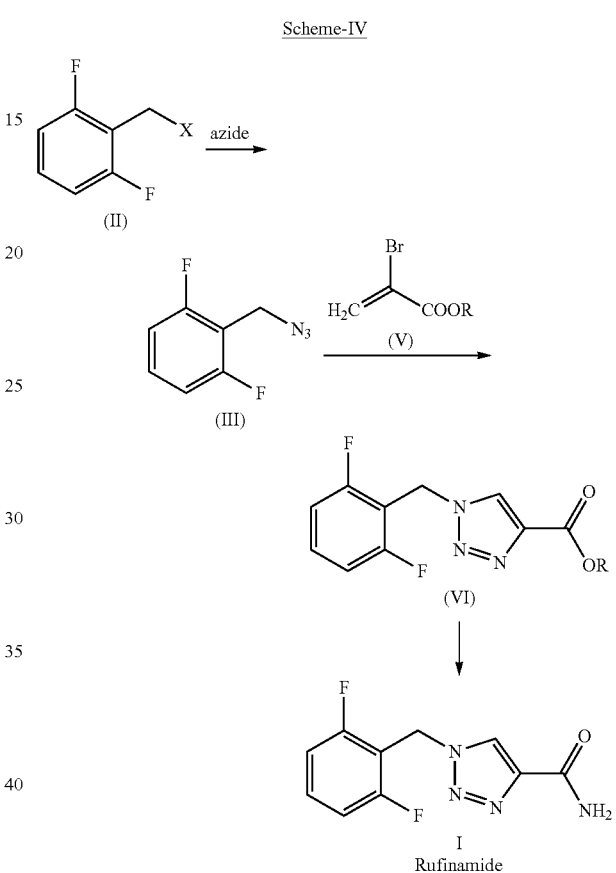

In the above scheme, 2-(azidomethyl)-1,3- difluorobenzyl of formula III

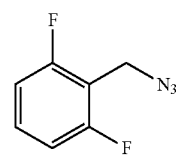

Formula-III is obtained by reacting the 2-(halomethyl)-1,3-difluorobenzene of formula II, wherein X is Cl, Br or I with an alkali metal azide reagent. The alkali metal azide may be selected from sodium azide, potassium azide; preferably the alkali metal azide is sodium azide. The reaction is carried out in a polar solvent selected from the group consisting of DMSO, DMF, t-butanol, preferably t-butanol to give the compound of the formula III. In an embodiment, 2-(bromomethyl)-1,3-difluorobenzene is treated with sodium azide in t-butanol to obtain 2-(azidomethyl)-1,3- difluorobenzyl of formula III.

The condensation of the compound of formula III with 2-bromoacrylate of formula V to obtain compound of formula VI.

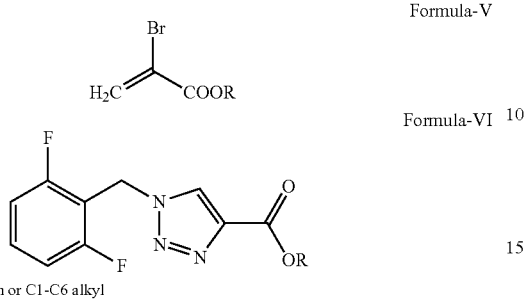

Formula-V

Formula-VI

R = hydrogen or C1-C6 alkyl

The invention relates in particular to the preparation of compound of formula VI in which R is hydrogen, methyl or ethyl by treating corresponding acrylates compound of formula V such as 2-bromoacrylic acid, methyl 2-bromoacrylate or ethyl 2-bromoacrylate with azide compound of formula III.

The invention relates primarily to the preparation of methyl 1-(2, 6-difluorobenzyl)-1H-1,2,3-triazole-4-carboxylate of formula VI.

The condensation of the azide compound of formula III with formula V is carried out in suitable polar protic solvent selected from the group consisting of acetic acid, methanol, formic acid, isopropanol, water and the like and mixtures thereof. The said reaction is carried out preferably in water or tert-butanol or mixtures thereof to give the compound of the formula VI.

In a preferred embodiment 2-(azidomethyl)-1,3- difluorobenzene is treated with methyl 2-bromoacrylate in mixture of t-butanol and water to produce methyl 1-(2,6-difluorobenzyl)-1H-1,2,3-triazole-4-carboxylate.

The 1-(2,6-difluorobenzyl)-1H-1,2,3-triazole-4-carboxylate ester, where R is C1-C6 alkyl, of formula VI can be directly converted to Rufinamide by treatment with ammonia or by other methods known in the prior art. The conversion can also be proceeded through 1-(2,6-difluorobenzyl)-1H-1,2,3-triazole-4-carboxylic acid intermediate, which in turn produced by hydrolysis of 1-(2,6-difluorobenzyl)-1H-1,2,3-triazole-4-carboxylate ester with alkali metal hydroxide.

In an preferred embodiment, methyl 1-(2,6-difluorobenzyl)-1H-1,2,3-triazole-4-carboxylate ester is hydrolysed in presence of aq. NaOH solution or NaOH flakes followed by acidification with HCl gives 1-(2,6-diflurobenzyl)-1H-1,2,3-triazole-4-carboxylic acid compound of formula VII.

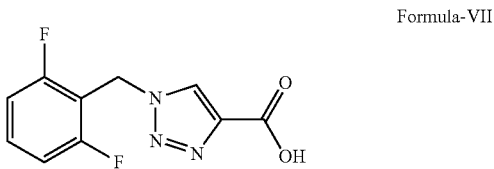 [SMILES: O=C(O)c1cn(Cc2c(F)cccc2F)nn1]

Formula-VII

Reaction of 1-(2,6-diflurobenzyl)-1H-1,2,3-triazole-4-carboxylic acid compound of formula VII, with chlorinating agents, preferably thionyl chloride, provides corresponding carbonyl chloride compound which is subsequently treated with ammonia to yield Rufinamide of formula I. The amidation reaction is done in presence of liquid or gaseous ammonia in a suitable solvent such as methanol, ethanol, propanol, toluene and the like and mixtures thereof; preferably toluene to give Rufinamide of formula I. The product is optionally purified from formic acid and methanol.

The present invention also provides process for the preparation of 2-bromoacrylate of formula V, which comprises brominating acrylate of formula IV in presence of a brominating agent followed by treatment with base.

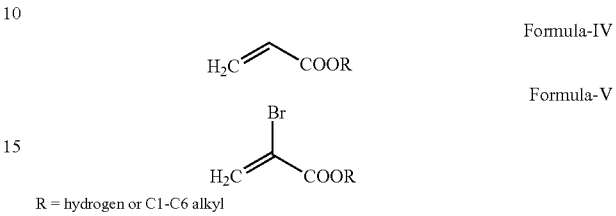

Formula-IV

Formula-V

R = hydrogen or C1-C6 alkyl

The invention relates in particular to the preparation of compound of formula V in which R is hydrogen, methyl or ethyl by brominating acrylic acid, methyl acrylate or ethyl acrylate of formula IV in presence of brominating agent. The invention relates primarily to the preparation of compound of formula V in which R is methyl by brominating methyl acrylate.

The bromination reaction can be carried out in presence of a reagent selected from the group consisting of phosphorus tribromide, aluminum tribromide, bromine and the like; in suitable aprotic solvent selected from the group consisting of THF, acetone, acetonitrile and MDC and the like. The base used in the bromination reaction is selected from the group consisting of sodium bicarbonate, potassium carbonate, potassium bicarbonate, potassium tert-butoxide, triethyl amine; preferably sodium carbonate and triethylamine, to give compound of the formula V. In a preferred embodiment methyl acrylate is brominated in presence of bromine and sodium carbonate in methylene chloride solvent to produce methyl 2-bromoacrylate.

The invention is further illustrated with following non-limiting examples:

EXAMPLES

Example-1

Preparation of Monobromo Methyl Acrylate

A mixture of Methyl acrylate (100 g) and methylene dichloride (300 ml) were cooled to 0-5° C. Bromine (60 ml) was added to the mixture at 0-5° C. for 1 hour. The contents were maintained for 4-5 hours at 25-30° C. 10% NaHCO$_3$ (100 ml) solution was charged to the above mixture and stirred for 30 minutes. The layers were separated. Sodium carbonate (250 gms) and triethylamine (160 ml) were added in methylene dichloride layer and stirred at 25-30° C. for 1 hour. The mixture was maintained for 2 hour at 25-30° C. and filtered. 20%. HCl solution (100 ml) was charged into filtrate and stirred for 30 minutes. The layer was separated and the organic layer was washed with 20% HCl solution (100 ml). The organic layer was distilled off completely under vacuum at below 30° C. Yield: 140 gms.

Example-2

Preparation of 2-(azidomethyl)-1,3-difluorobenzene

A mixture of 2,6-diflourobenzyl bromide (100 gms), tetrabutylammonium bromide (10 gms), t-butanol (200 ml) and sodium azide (62.8 gm) were stirred at room temperature for 22-24 hours. After the completion, reaction mass was filtered and washed with t-butanol (2.5 ml) to give 2-(azidomethyl)-1,3-difluorobenzene.

Example-3

Preparation of methyl 1-(2,6-difluorobenzyl)-1H-1,2,3-triazole-4-carboxylate A mixture of 2-(azidomethyl)-1,3-difluorobenzene in t-butanol prepared as per example 2, methyl 2-bromoacrylate (120 gms) and water (200 ml) were heated to 75-80° C. The contents was stirred at 75-80° C. for 24 hours. After the completion of reaction, the reaction mixture was cooled to room temperature. The solid obtained was filtered and then crude mass was added to cyclohexane (240 ml) and the mixture was stirred at room temperature for 2 hours. The solid was filtered and washed with cyclohexane (50 ml). The product was dried for 2 hours to give methyl 1-(2,6-difluorobenzyl)-1H-1,2,3-triazole-4-carboxylate. Yield: 120 gms

Example-4

Preparation of 1-(2,6-difluorobenzyl)-1H-1,2,3-triazole-4-carboxylic acid

A mixture of Methyl 1-(2,6-difluorobenzyl)-1H-1,2,3-triazole-4-carboxylate. (50 gms) and a solution of sodium hydroxide (11.76 gms in 100 ml water) were stirred at room temperature contents till it becomes clear. Hydrochloric acid (30 ml) in DM water (70 ml) was charged to above reaction mass. Adjusted the PH of the reaction till 2-3 by adding the hydrochloric acid solution at 25-30° C. After the completion, reaction mass was filtered and dried the material at 65° C.-70° C. for 15 hours. Yield: 40 gms

Example 5

Preparation of Rufinamide

A mixture of 1-(2,6-difluorobenzyl)-1H-1,2,3-triazole-4-carboxylic acid (25 gms) and thionyl chloride (63.5 gms) were stirred at 80° C. and maintained for 3 hours. The reaction mass was cooled to 50° C. and excess thionyl chloride was distilled off. To this reaction mass toluene (25 ml) was charged twice and it was distilled off under vacuum it was followed by addition of toulene (175 ml) to get clear solution. Aqueous ammonia (100 ml) charged into reaction mass at room temperature and maintained for 2 hours. The reaction mass was filtered. 10% sodium carbonate solution was added to above solid and stirred for 30 minutes. The solid was filtered and washed with water and cyclohexane (50 ml). Dried the crude material in a vacuum oven at 70-80° C. for 10 hours. Yield: 23.00 gm.

Example 6

Purification of Rufinamide

Crude Rufinamide (7.5 gm) and formic acid (36 ml) were heated to 50-55° C. to get a clear solution. It was added to methanol over 2 hours at 20-25° C. Methanol (37.5 ml) was added to the reaction mass at 20-25° C. After addition the reaction mass was stirred for 2 hours at 20-25° C. The solid was filtered and washed with methanol (75 ml). The solid was dried at 60° C. under vacuum. Yield: 6.3 gms.

We claim:
1. A process for preparing Rufinamide of formula I

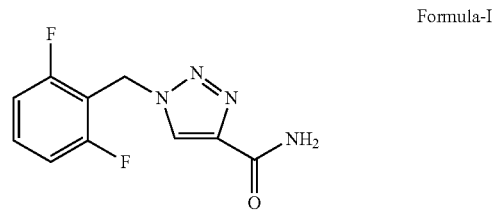 [SMILES: NC(=O)c1cn(Cc2c(F)cccc2F)nn1]

Formula-I comprising the steps of:
(a) reacting a compound of formula III

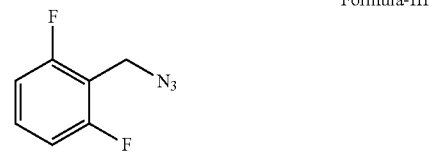

Formula-III with 2-bromoacrylate of formula V to obtain a compound of formula VI

Formula-V

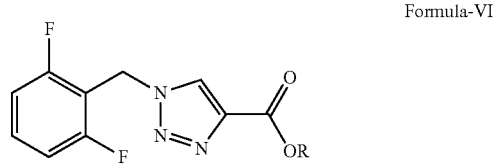

Formula-VI wherein R is hydrogen or a C1-C6 alkyl group; and
(b) converting the compound of formula VI to Rufinamide of formula I.

2. The process according to claim 1, wherein R is hydrogen, methyl or ethyl.

3. The process according to claim 1, wherein the compound of formula V is selected from 2-bromoacrylic acid, methyl 2-bromoacrylate and ethyl 2-bromoacrylate.

4. The process according to claim 1, wherein the compound of formula VI prepared in step (a) is methyl 1-(2, 6-difluorobenzyl)-1H-1, 2, 3-triazole-4-carboxylate.

5. The process according to claim 1 wherein the compound of formula V is prepared by a method comprising the steps of:
Br
Formula—V
brominating a compound of formula IV in the presence of a brominating agent followed by treatment with base,

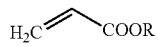

Formula-IV wherein the R group of formula IV is hydrogen or C1-C6alkyl group.

6. The process according to claim 5, wherein R is H, methyl or ethyl.

7. The process according to claim 6, wherein R is methyl.

8. The process according to claim 5, wherein the brominating agent is selected from the group consisting of phosphorus tribromide, aluminum tribromide and bromine.

9. The process according to claim 8, wherein the brominating agent is bromine.

10. The process according to claim 5, wherein the base is selected from the group consisting of sodium carbonate, sodium bicarbonate, potassium carbonate, potassium bicarbonate, potassium t-butoxide and triethylamine.

11. The process according to claim 10, wherein the base is selected from sodium carbonate and triethylamine.

12. The process according to claim 5, wherein methyl 2-bromoacrylate is prepared.

13. The process of claim 1, further comprising the step of purifying the Rufinamide obtained in step (b).

* * * * *